United States Patent
Michaels

(10) Patent No.: US 9,364,415 B2
(45) Date of Patent: Jun. 14, 2016

(54) ASCORBIC ACID-BASED IODINE STAIN REMOVER AND METHOD OF USE

(71) Applicant: Basil Michaels, Richmond, MA (US)

(72) Inventor: Basil Michaels, Richmond, MA (US)

(*) Notice: Subject to any disclaimer, the term of this patent is extended or adjusted under 35 U.S.C. 154(b) by 0 days.

(21) Appl. No.: 14/213,262

(22) Filed: Mar. 14, 2014

(65) Prior Publication Data

US 2015/0257999 A1 Sep. 17, 2015

(51) Int. Cl.
| | |
|---|---|
| *C11D 3/48* | (2006.01) |
| *C11D 7/08* | (2006.01) |
| *A61Q 5/02* | (2006.01) |
| *A61Q 19/10* | (2006.01) |
| *A61K 8/67* | (2006.01) |

(52) U.S. Cl.
CPC ............. *A61K 8/676* (2013.01); *A61Q 19/10* (2013.01); *A61Q 5/02* (2013.01)

(58) Field of Classification Search
CPC ........ C11D 3/48; C11D 7/08; C11D 11/0094; C11D 17/003; C11D 17/0043; A61Q 5/02; A61Q 19/005; A61Q 19/10
See application file for complete search history.

(56) References Cited

U.S. PATENT DOCUMENTS

| | | | | |
|---|---|---|---|---|
| 2001/0006661 | A1* | 7/2001 | Kaneda et al. | 424/400 |
| 2004/0091616 | A1* | 5/2004 | Smith et al. | 427/234 |
| 2004/0151684 | A1* | 8/2004 | Mori et al. | 424/70.14 |
| 2007/0218562 | A1* | 9/2007 | Li et al. | 436/106 |
| 2008/0254130 | A1* | 10/2008 | Gupta | 424/489 |
| 2009/0143268 | A1* | 6/2009 | Genkin et al. | 510/137 |
| 2011/0262558 | A1* | 10/2011 | Huckfeldt et al. | 424/618 |
| 2014/0079660 | A1* | 3/2014 | Doi | 424/70.24 |

FOREIGN PATENT DOCUMENTS

WO   92/04659   * 3/1992

OTHER PUBLICATIONS http://www.removeallstains.com/2014/11/how-to-remove-iodine-stains-from-skin_13.html#.VcDxv03bLDA.*
https://answers.yahoo.com/question/index?qid=20070713154047AAd8KDR.*
https://answers.yahoo.com/question/index?qid=20110503175457AAbEnKf.*
http://www.earthclinic.com/remedies/iodine10.html.*

* cited by examiner

*Primary Examiner* — Charles Boyer

(74) *Attorney, Agent, or Firm* — Hamilton, Brook, Smith & Reynolds, P.C.

(57) ABSTRACT

Described herein are methods for removing an iodine stain from a surface. In one embodiment, the method comprises contacting an iodine-stained surface with ascorbic acid for a period of time sufficient to remove the iodine stain from the surface, thereby removing the iodine stain from the surface.

8 Claims, No Drawings

ASCORBIC ACID-BASED IODINE STAIN REMOVER AND METHOD OF USE

BACKGROUND

Iodine antiseptics are widely used in the healthcare industry for the prevention and treatment of skin infections and the treatment of wounds. For example, surgeons regularly apply an iodine antiseptic to patients pre-operation to prepare the skin prior to surgery.

Iodine stains, for example, those left behind by iodine antiseptics, are notoriously difficult to remove and fade very slowly. Iodine staining of human skin and hair is particularly problematic, and the few products available for iodine stain removal are not safe for use on the human body.

SUMMARY OF THE INVENTION

As iodine stains are problematic, it is desirable to find a cost effective and efficient stain solution that can be used to safely and effectively remove iodine stains, particularly iodine stains on the human body.

The present invention is based on the unexpected discovery that ascorbic acid, when applied to an antiseptic iodine stain on human skin, removes the iodine stain quickly and effectively.

In one embodiment, a method for removing an iodine stain from a surface is provided. The method comprises contacting an iodine stain on a surface with ascorbic acid for a period of time sufficient to remove the iodine stain from the surface, thereby removing the iodine stain from the surface.

Another embodiment is a method for removing an iodine stain from a human or animal body, comprising applying a mixture comprising ascorbic acid in a medium to an iodine stain on a human or animal body; and allowing the mixture to contact the iodine stain for a period of time sufficient to remove the iodine stain from the human or animal body, thereby removing the iodine stain from the human or animal body.

Yet another embodiment is a method for removing an iodine antiseptic stain from a human or animal body, comprising applying a mixture comprising ascorbic acid in a medium to an iodine antiseptic stain on a human or animal body; and allowing the mixture to contact the iodine antiseptic stain for a period of time sufficient to fade or remove the iodine antiseptic stain from the human or animal body, thereby removing the iodine antiseptic stain from the human or animal body.

The methods described herein can be used safely, rapidly and effectively to remove iodine stains from a variety of surfaces. Unexpectedly, when applied to an iodine stain on the human skin, ascorbic acid does not cause skin irritation or other adverse reactions.

DETAILED DESCRIPTION OF THE INVENTION

A description of example embodiments of the invention follows.

A first embodiment is a method for removing an iodine stain from a surface. The method comprises contacting an iodine stain on a surface with ascorbic acid for a period of time sufficient to remove the iodine stain from the surface, thereby removing the iodine stain from the surface.

"Iodine stain," as used herein, refers to an area of coloration or discoloration on a surface that is due to the surface having been in contact with iodine. An iodine stain includes both coloration or discoloration of a surface indicating the continued presence of iodine on the surface, as well as coloration or discoloration of a surface left behind by iodine. An iodine stain can be a variety of colors, but is typically yellowish, orangey or brownish in color.

"Removing an iodine stain," as used herein, includes both the complete and partial removal of an iodine stain from a surface. Partial removal of an iodine stain from a surface includes both the removal of the stain (complete or partial) from a portion of the stained area as well as fading or dulling of the stain in general.

Iodine stains are particularly prevalent in healthcare settings, where iodine is frequently used as a disinfectant and antiseptic. Therefore, in some embodiments, the iodine stain is an iodine antiseptic stain. "Iodine antiseptic," as used herein, refers to any iodine-based formulation designed to be applied to the human body to treat or prevent infection or to reduce the likelihood of infection. Exemplary iodine antiseptics include, but are not limited to, povidone-iodine, iodine povacrylex, tincture of iodine and Lugol's iodine.

Ascorbic acid (also known as vitamin C) undergoes an oxidation-reduction reaction in the presence of iodine to produce dehydroascorbic acid and iodide, which typically lack the pigmentation associated with iodine. Because of the relatively non-toxic nature of both ascorbic and dehydroascorbic acid, the types of surfaces that can be safely contacted with ascorbic acid in the methods of the invention are vast. For example, in some embodiments, the surface is a human or animal body; a hard surface (e.g., tile, ceramic, flooring); clothing; linen (e.g., towels, bedsheets); carpet; or upholstery, or a combination of two or more of any of the foregoing. Many of the surfaces contacted with ascorbic acid in the methods described herein are present in healthcare settings, for example, hospitals or surgical centers, where the methods are likely to be used.

In a specific embodiment, the surface is a human or animal body. In a more specific embodiment, the surface is a human body. Particular examples of surfaces of the human or animal body that can be contacted with ascorbic acid in the methods of the invention include skin or hair, or a combination thereof. In one embodiment, the surface is human skin or human hair, or a combination thereof.

As used herein, "animal" refers to veterinary animals and excludes humans. Veterinary animals include domestic animals, for example, but not limited to, dogs, cats, horses, and cattle.

Under many conditions, the reaction between ascorbic acid and iodine is very rapid. Thus, a period of time sufficient to remove an iodine stain is often a very short period of time. For example, a povidone-iodine stain on human skin disappears virtually upon contact with an aqueous solution of ascorbic acid. One skilled in the art relevant art will be able to determine when a sufficient period of time has elapsed.

An adequate amount of ascorbic acid to remove the stain can be determined empirically (because the reaction between ascorbic acid and iodine is typically so rapid). An adequate amount of ascorbic acid is an amount sufficient to remove the iodine stain (e.g., to convert all of the iodine in the iodine stain to iodide, to completely remove or fade or dull the iodine stain). Thus, in some embodiments of the methods described herein, an amount of ascorbic acid or an amount of a mixture comprising ascorbic acid sufficient to remove the iodine stain is applied to or brought into contact with the iodine stain.

Typically, the ascorbic acid used in the methods described herein is provided as a mixture of ascorbic acid in a medium. Thus, in some embodiments, the method comprises contacting an iodine stain on a surface with a mixture comprising ascorbic acid in a medium for a period of time sufficient to fade or remove the iodine stain from the surface, thereby removing the iodine stain from the surface.

In some embodiments, the medium of the mixture comprising ascorbic acid in a medium is selected from the group consisting of an organic solvent and an aqueous medium, or a mixture thereof. Non-limiting examples of organic solvents include polar organic solvents (e.g., dimethylsulfoxide, dimethylformamide) and alcohols (e.g., methanol, ethanol, isopropanol). Non-limiting examples of aqueous solvents include water and buffered aqueous solutions (e.g., phosphate-buffered saline) of various pH levels. Non-limiting examples of mixtures of an organic solvent and an aqueous medium include organic-organic mixtures (e.g., methanol-dimethylsulfoxide) and organic-aqueous mixtures (e.g., methanol-water, buffer-dimethylsulfoxide). If the ascorbic acid is provided as a mixture in one or more organic solvents or as a mixture in an organic-aqueous mixture and is intended for use on the human or animal body, the amount of organic solvent in the mixture should not exceed a level that is safe for contact with human or animal tissues or skin, respectively. Similarly, if the ascorbic acid is provided as a mixture in an aqueous medium or an organic-aqueous mixture and is intended for use on the human or animal body, the amount of any additive in the medium should not exceed a level that is safe for contact with human or animal tissues or skin, respectively.

In a particular embodiment, the ascorbic acid is provided as an aqueous solution, for example, an aqueous saline solution.

The mixture comprising ascorbic acid in a medium can be in the form of a gel, a lotion, a foam or a rinse. Further, the mixture can include one or more additives or preservatives, for example, to increase the stability of the mixture or to regulate the pH of the mixture. Buffers, for example, can be used to regulate the pH of an aqueous or organic-aqueous mixture comprising ascorbic acid.

It may often be convenient to apply ascorbic acid (e.g., a mixture comprising ascorbic acid in a medium) to a surface to remove an iodine stain from the surface. Therefore, in some embodiments, the method of removing an iodine stain from a surface comprises applying ascorbic acid to an iodine stain on a surface; and allowing the ascorbic acid to contact the iodine stain for a period of time sufficient to remove the iodine stain from the surface, thereby removing the iodine stain from the surface.

In some embodiments, the mixture comprising ascorbic acid in a medium is designed to be sprayed onto a surface. Thus, in some embodiments, the method comprises spraying an iodine stain on a surface with a mixture comprising ascorbic acid in a medium; and allowing the mixture to contact the iodine stain on the surface for a sufficient period of time to remove the iodine stain from the surface.

After contacting an iodine stain with ascorbic acid for a period of time sufficient to remove the iodine stain, or after allowing ascorbic acid to contact an iodine stain for a period of time sufficient to remove the iodine stain, the area contacted with the ascorbic acid can be rinsed (e.g., with water or soap and water) and/or dried. Thus, in some embodiments, the methods described herein further comprise rinsing and/or drying (e.g., rinsing, drying or rinsing and drying) an area of the surface contacted with ascorbic acid or a mixture comprising ascorbic acid. For example, if ascorbic acid is provided as an aqueous solution, it may be convenient to dry the area of the surface from which the iodine stain has been removed after a period of time sufficient to remove the iodine stain has elapsed. In embodiments in which the surface is a human or animal body, the methods can further comprise rinsing and/or drying an area of the human or animal body contacted with ascorbic acid or a mixture comprising ascorbic acid.

A further embodiment is a method for removing an iodine stain from a human or animal body. The method comprises applying a mixture comprising ascorbic acid in a medium to an iodine stain on a human or animal body; and allowing the mixture to contact the iodine stain for a period of time sufficient to remove the iodine stain from the human or animal body, thereby removing the iodine stain from the human or animal body.

In some embodiments of a method for removing an iodine stain from a human or animal body, the method is a method of removing an iodine stain from a human body and the method comprises applying a mixture comprising ascorbic acid in a medium to an iodine stain on a human body; and allowing the mixture to contact the iodine stain for a period of time sufficient to remove the iodine stain from the human body, thereby removing the iodine stain from the human body.

The method of removing an iodine stain from a human or animal body can also be a method of removing an iodine stain from human skin or human hair or a combination thereof. The method of removing an iodine stain from human skin or human hair comprises applying a mixture comprising ascorbic acid in a medium to an iodine stain on human skin or human hair or a combination thereof; and allowing the mixture to contact the iodine stain for a period of time sufficient to remove the iodine stain from the human skin or human hair or combination thereof, thereby removing the iodine stain from the human skin or human hair or combination thereof Yet a further embodiment is a method for removing an iodine antiseptic stain from a human or animal body. The method comprises applying a mixture comprising ascorbic acid in a medium to an iodine antiseptic stain on a human or animal body; and allowing the mixture to contact the iodine antiseptic stain for a period of time sufficient to fade or remove the iodine antiseptic stain from the human or animal body, thereby removing the iodine antiseptic stain from the human or animal body.

In some embodiments of a method for removing an iodine antiseptic stain from a human or animal body, the method is a method of removing an iodine antiseptic stain from a human body and the method comprises applying a mixture comprising ascorbic acid in a medium to an iodine antiseptic stain on a human body; and allowing the mixture to contact the iodine antiseptic stain for a period of time sufficient to fade or remove the iodine antiseptic stain from the human body, thereby removing the iodine antiseptic stain from the human body.

The method of removing an iodine antiseptic stain from a human or animal body can also be a method of removing an iodine antiseptic stain from human skin or human hair or a combination thereof. The method of removing an iodine antiseptic stain from human skin or human hair comprises applying a mixture comprising ascorbic acid in a medium to an iodine antiseptic stain on human skin or human hair or a combination thereof; and allowing the mixture to contact the iodine antiseptic stain for a period of time sufficient to remove the iodine antiseptic stain from the human skin or human hair or combination thereof, thereby removing the iodine antiseptic stain from the human skin or human hair or combination thereof The iodine antiseptic in the methods described herein can be povidone-iodine, iodine povacrylex, tincture of iodine or Lugol's iodine. In a particular embodiment, the iodine antiseptic is povidone-iodine.

EXEMPLIFICATION

A cream containing ascorbic acid was applied to a human patient's skin. Subsequently, povidone-iodine was applied to the same area of the patient's skin that had been exposed to the cream containing ascorbic acid. The povidone-iodine did not stain the patient's skin.

An aqueous solution of ascorbic acid was applied to an area of a human patient's skin stained by povidone-iodine. Application of the aqueous solution of ascorbic acid removed the povidone-iodine stain on the patient's skin.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for rendering a surface resistant to iodine coloration or discoloration, the method comprising:
    applying an ascorbic acid delivery agent to a surface, the surface being at least one of skin, hair or a combination thereof; the ascorbic acid delivery agent being a mixture comprising ascorbic acid in a medium; and
    allowing the delivery agent to react with the surface for a duration of time determined to be sufficient for rendering the surface resistive to iodine coloration or discoloration, thereby rendering the surface resistive to iodine coloration or discoloration from the subsequent application of iodine.

2. The method of claim 1, wherein the iodine coloration or discoloration is an iodine antiseptic coloration or discoloration.

3. The method of claim 2, wherein the iodine antiseptic is povidone-iodine, iodine povacrylex, tincture of iodine or Lugol's iodine.

4. The method of claim 1, wherein the surface is a human or animal body.

5. The method of claim 1, wherein the medium is selected from the group consisting of an organic solvent and an aqueous medium, or a mixture thereof.

6. The method of claim 5, wherein the ascorbic acid is provided as an aqueous solution.

7. The method of claim 1, wherein the mixture is in the form of a gel, a lotion, a foam or a rinse.

8. The method of claim 1, wherein the mixture is designed to be sprayed onto the surface.

* * * * *